United States Patent [19]
Kowalski et al.

[11] Patent Number: 5,459,677
[45] Date of Patent: Oct. 17, 1995

[54] CALIBRATION TRANSFER FOR ANALYTICAL INSTRUMENTS

[75] Inventors: Bruce R. Kowalski, Issaquah; David J. Veltkamp; Yong D. Wang, both of Seattle, all of Wash.

[73] Assignee: Board of Regents of the University of Washington, Seattle, Wash.

[21] Appl. No.: 720,256

[22] Filed: Jun. 24, 1991

Related U.S. Application Data

[63] Continuation-in-part of Ser. No. 595,458, Oct. 9, 1990, abandoned.

[51] Int. Cl.$^6$ .................................................. G01N 21/01
[52] U.S. Cl. ........................... 364/571.02; 250/252.1; 73/1 R; 364/498
[58] Field of Search .................. 364/571.04, 571.02, 364/497, 498; 250/252.1; 73/1 R

[56] References Cited

U.S. PATENT DOCUMENTS

| | | | |
|---|---|---|---|
| 3,975,727 | 8/1976 | Mader et al. | 73/1 R X |
| 4,587,624 | 5/1986 | Banno | 364/571.04 |
| 4,660,151 | 4/1987 | Chipman et al. | 364/498 |
| 4,864,842 | 9/1989 | Regimand | 364/571.04 X |
| 4,866,644 | 9/1989 | Shenk et al. | 364/571.02 |
| 4,916,645 | 4/1990 | Wuest et al. | 364/571.04 |
| 5,016,203 | 5/1991 | Komatsu et al. | 364/571.02 |

OTHER PUBLICATIONS

Camo Inc., "Computer–Aided Engineering Software for Multivariate Analysis, Calibration and Prediction Introduced by Camo, Inc.," News Release, Dec. 19, 1988, 2 pages.
Guided Wave, Inc., News Release about a software package for use with spectrophotometers, Nov. 21, 1988, 1 page.
D. Honigs, "Near Infrared Analysis," Analytical Instrumentation, vol. 14, No. 1, 1985, pp. 1–48.
J. Kelly, C. Barlow, T. Jinguji & J. Callis, "Predication of Gasoline Octane Numbers from Near–Infrared Spectral Features in the Range 660–1215 nm," Analytical Chemistry, No. 61, pp. 313–320.
A. Lorber & B. Kowalski, "A Note on the Use of the Partial Least–Squares Method for Multivariate Calibration," Applied Spectroscopy, vol. 42, No. 8, 1988, pp. 1572–1574.
LT Industries, Inc., News Release, "LT Industries Unveils Powerful Software for NIR Analysis," Dec. 11, 1989, 2 pages.
LT Industries, Inc., News Release, "High–Speed NIR Analyzer for Non–Destructive, On–Line, Multi–Constituent Monitoring to be Featured at Pittcon," Feb. 12, 1990, 3 pages.

(List continued on next page.)

*Primary Examiner*—Emanual T. Voeltz
*Assistant Examiner*—Edward Pipala
*Attorney, Agent, or Firm*—Christensen, O'Connor, Johnson & Kindness

[57] ABSTRACT

A technique for transferring a multivariant calibration model from a reference analytical instrument to a target analytical instrument that may be a different instrument, or the same instrument at a later time. In a "direct" approach, a plurality of transfer samples are selected, and a plurality of measurements are made for each transfer sample using the reference instrument, producing a reference instrument response for each sample. These measurements are repeated for the target instrument, to produce a target instrument response for each transfer sample. One then generates transfer coefficients capable of performing a multivariate estimation of the reference instrument responses for the transfer samples from the target instrument responses for those samples. The transfer coefficients may then be used to convert a target instrument response for an unknown sample into the equivalent response for the reference instrument. In an important "piecewise" variation, the transfer coefficients comprise a plurality of estimation coefficients for estimating each reference data value from more-than-one but less-than-all target data values. "Classical" and "inverse" transfer techniques are also described, wherein target instrument responses for the transfer samples are combined with reference instrument responses for the full set of calibration samples, to derive a multivariate prediction model for the target instrument.

18 Claims, 9 Drawing Sheets

OTHER PUBLICATIONS

H. Mark & J. Workman, Jr., "A New Approach to Generating Transferable Calibrations for Quantitative Near–Infrared Spectroscopy," Spectroscopy, vol. 3, No. 11, pp. 28–36.

T. Naes, "Comparison of Approaches to Multivariate Linear Calibration," Biomedical Journal, vol. 27, No. 3, 1985, pp. 265–275.

T. Naes, "Multivariate Calibration Using Covariance Adjustment," Biomedical Journal, vol. 28, No. 1, pp. 99–107.

B. Osborne, "Calibration of Instruments for Near–Infrared Spectroscopy," Spectroscopy, vol. 4, No. 4, pp. 48–55.

B. Osborne & T. Fearn, "Collaborative evaluation of universal calibrations for the measurement of protein and moisture in flour by near infrared reflectance," Blackwell Scientific Publications, 1983, 5 pages.

E. Sanchez & B. Kowalski, "Tensorial Calibration: I. First–Order Calibration," Journal of Chemometrics, vol. 2, 1988, pp. 247–263.

J. Shenk, M. Westerhaus & W. Templeton, Jr., "Calibration Transfer Between Near Infrared Reflectance Spectrophotometers," Crop Science, vol. 25, Jan.–Feb. 1985, pp. 159–161.

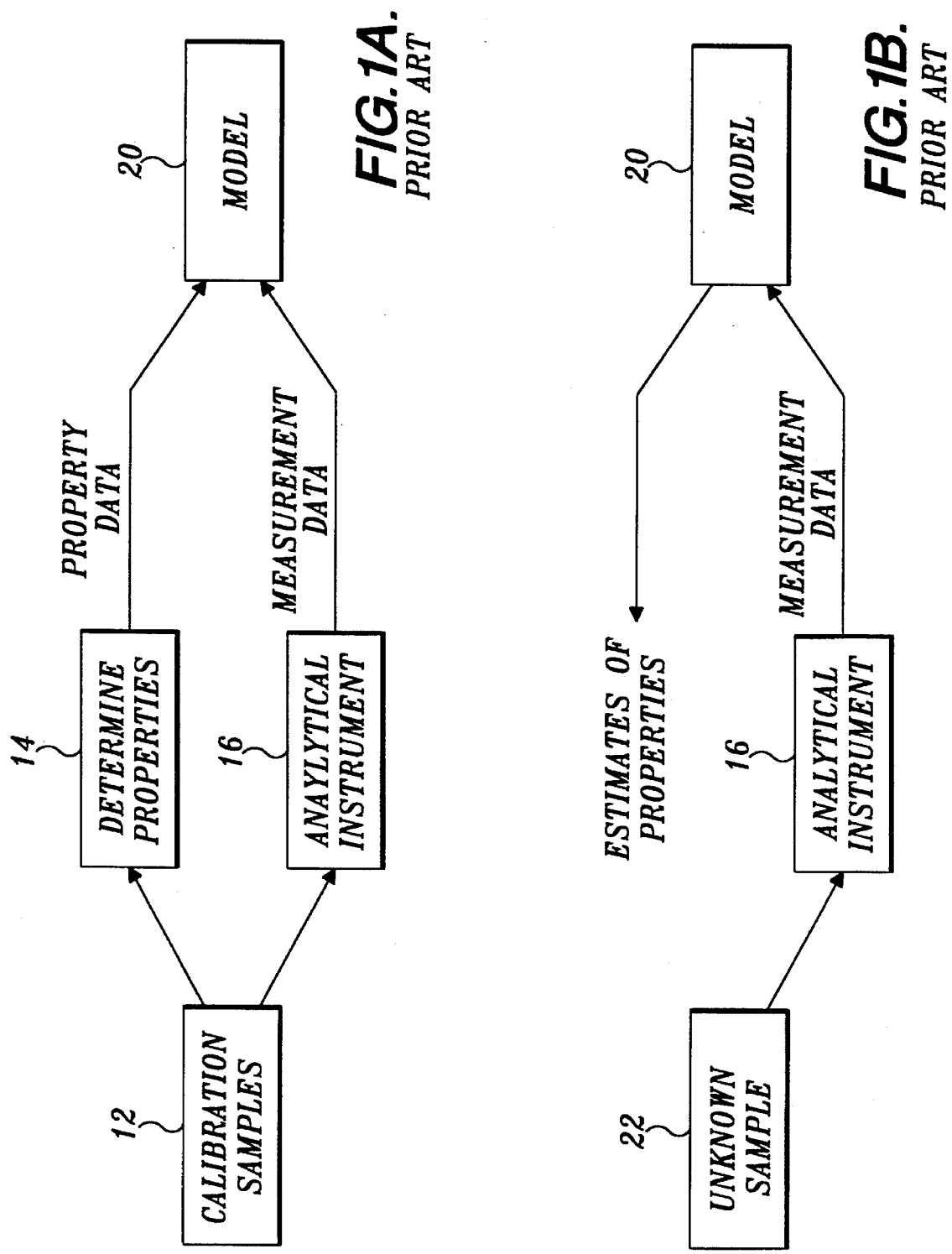

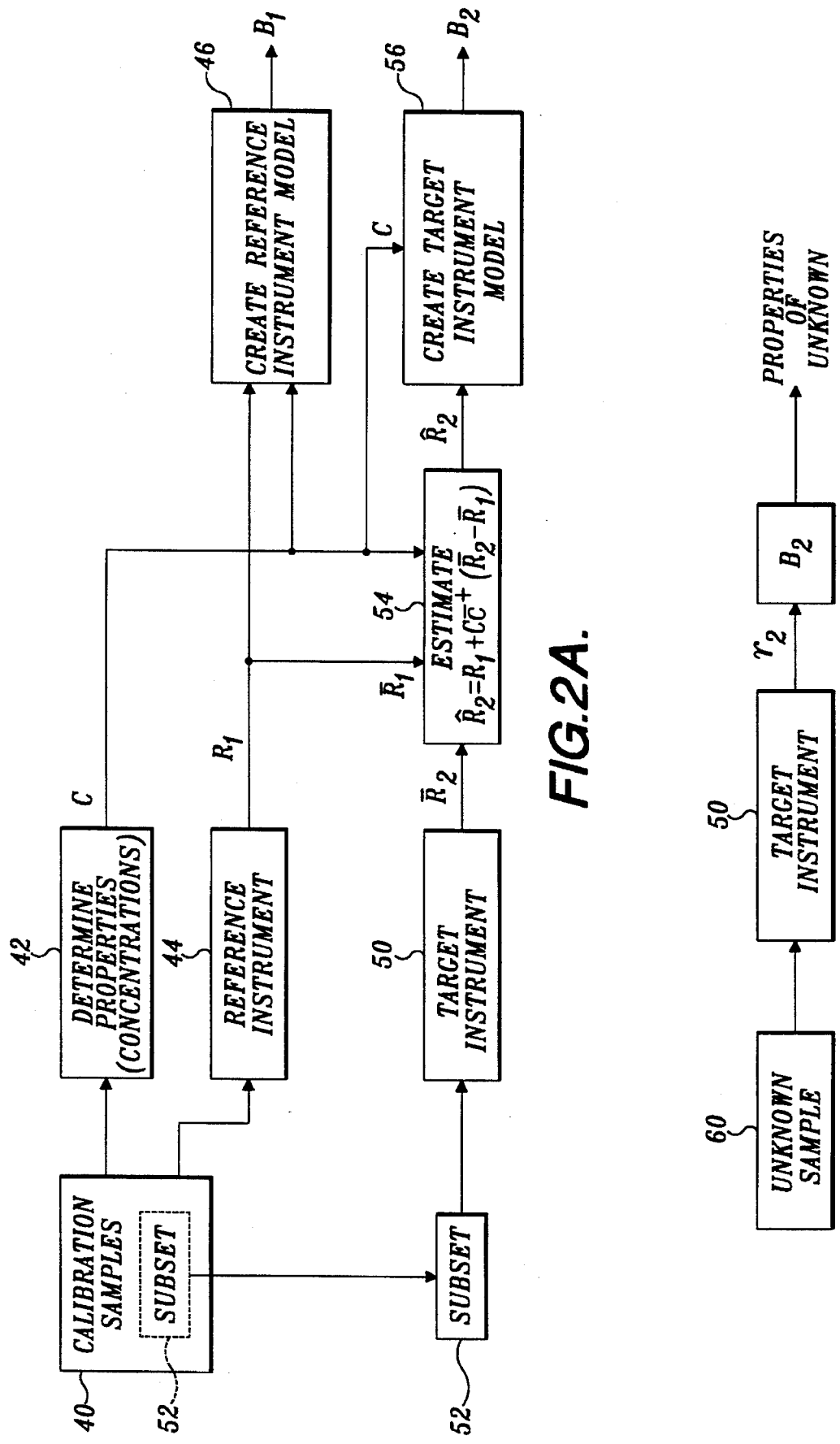

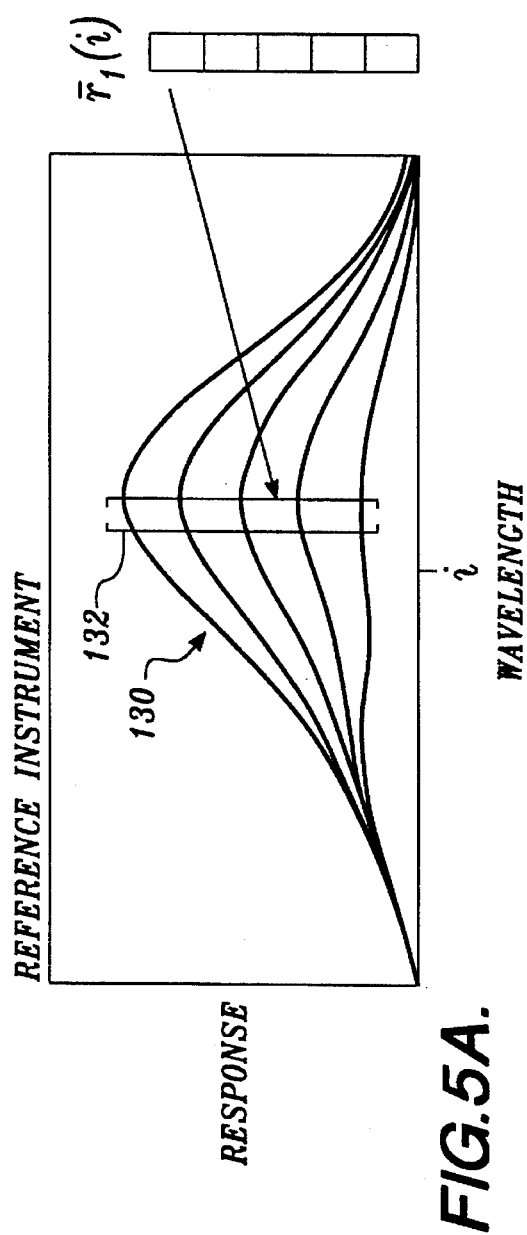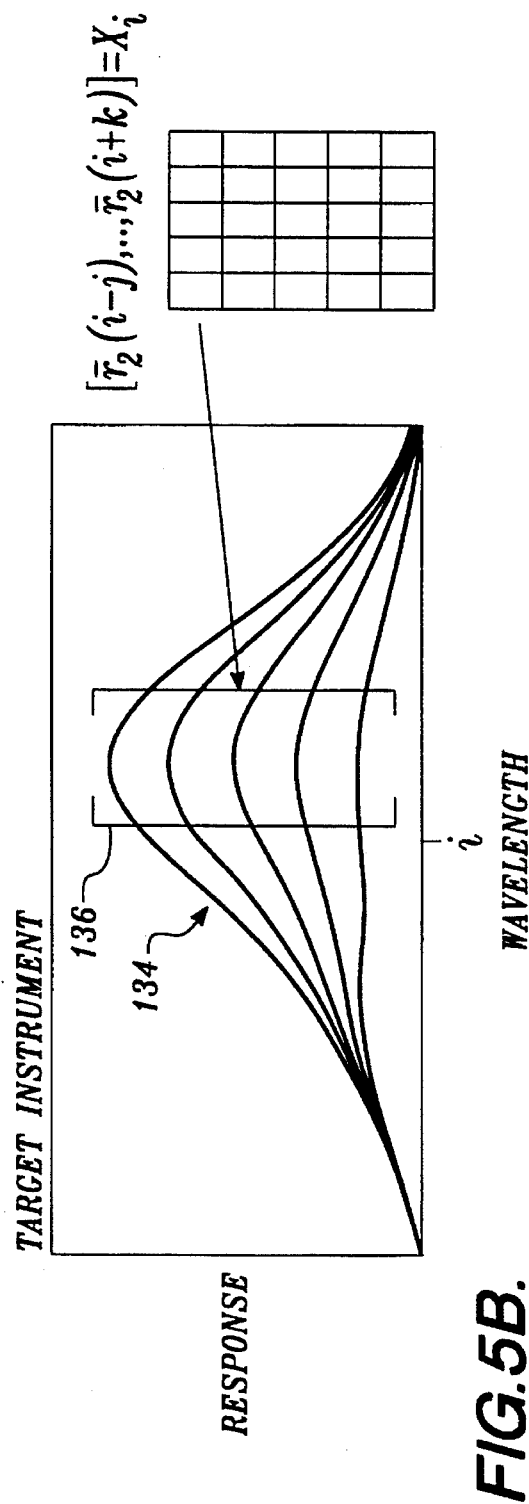
FIG.5A.
FIG.5B.

CALIBRATION TRANSFER FOR ANALYTICAL INSTRUMENTS

This invention was made with government support under grant No. EEC84-15075 awarded by the National Science Foundation. The government has certain rights in the invention. This application is a continuation in part of U.S. Ser. No. 07/595,458, filed Oct. 9, 1990, now abandoned.

FIELD OF THE INVENTION

The present invention relates to techniques for the calibration of analytical instruments such as spectrophotometers.

BACKGROUND OF THE INVENTION

The analytical chemist is frequently confronted with the problem of analyzing a sample to identify one or more properties of the sample, such as the octane number of a gasoline sample, or the protein content of a wheat sample. A closely related problem is the analysis of a sample to identify some or all of its constituents, and to determine their concentrations. The concentration of a given constituent can be regarded as a chemical property of the sample.

On many occasions, an instrument such as an absorption spectrophotometer is used to analyze the sample. However, instruments respond with signals (e.g. voltages or current), not reports of properties. Therefore a relationship has to be built that relates responses to properties before the instrument can be used to analyze samples. The process of building a model for the prediction of the properties of a sample from the instrument's responses is called calibration.

The advantages flowing from a successful model can be considerable. Imagine for example that it was desired to measure the concentration of a certain chemical species (analyte) in a chemical process stream. The most direct measurement technique would be to extract a sample from the process stream, and subject the sample to traditional chemical analysis techniques, to determine the analyte concentration. However, such an approach is cumbersome, and does not provide real time information. However, if a model can be constructed that relates the unknown concentration to absorbence of light at one or more wavelengths, a significant simplification would result. Concentration could then be estimated by placing a suitable optical absorbence measuring device in the process stream itself, thereby providing an efficient and real time technique for estimating the analyte's concentration.

An example of a calibration model is the classical calibration curve. The responses of an instrument are measured with a set of standard samples (calibration standards) of known analyte concentration. Such a set of calibration standards will be referred to herein as a calibration set. If a linear model is appropriate, then the response r measured by the instrument can be written $$r = b_1 c + b_0 \quad (1)$$

where c is the concentration of the analyte of interest, and the constants $b_1$ and $b_0$ are the model parameters. This is a univariate problem, in that the instrument response r is assumed to be a function of a single variable c. To calibrate the instrument, the instrument response r is measured for each sample in the calibration set, each such sample having a known concentration c. A linear least squares regression technique may then be used to determine the values of the constants $b_1$ and $b_0$ that provide the best fit of Equation (1) to the measured data. Once the model parameters are determined, concentrations of future samples may be estimated from the model, based upon the measured instrument response r.

Such univariate calibration requires that the instrument response be dependent only on the concentration of the analyte of interest. In order to fulfill this condition, the analytical chemist either separates the analyte from other constituents of the sample that interfere with the instrument response, or uses a highly selective instrument. Thus classical univariate calibration demands that the chemist make certain that there are no interfering species. If inadvertently an interfering constituent is present, there is no way to detect the error, much less to correct it.

Unfortunately, it is rarely possible to find univariate models that provide useful real world information. For example, it is generally the case that light absorbence at any given wavelength is affected by many chemical species that may be present, by turbidity, etc. In this more common case, the problem is multivariate, i.e., the measurable absorbence is a function of multiple variables, and multivariate calibration must be used to obtain reliable estimates of the property of interest. The use of multivariate calibration of analytical instruments is a rapidly growing field, primarily due to the development of so-called biased multivariate regression methods, such as principal component regression (PCR) and partial leased squares (PLS).

A standard multivariate calibration technique is illustrated in schematic form in FIGS. 1a and 1b. The technique begins with the preparation of a plurality of calibration samples 12. The calibration samples are formulated such that they are typical examples of the material, e.g., process stream, that the model will be used to analyze. One or more properties of interest for each calibration sample are then determined, as indicated in block 14, to produce "property" data representing such properties. In the ease of a physical property such as octane number, an analytic technique of accepted reliability and accuracy is used to measure the octane number for each calibration sample. In the ease where the properties are the concentrations of different chemical species, the concentrations may simply be recorded during the preparation of the samples. One then performs a plurality of measurements of each calibration sample, using analytical instrument 16, to produce "measurement" data. For example, for the ease in which the analytical instrument is a spectrophotometer, the absorbence of each sample is measured at a plurality of different wavelengths. Then, using any multivariate calibration method (e.g., principle component regression, partial least squares regression), one combines the property data produced in step 14 with the measurement data produced by analytical instrument 16, to obtain a model 20, i.e., a mathematical relationship, between the measured absorbence and the property or properties of interest.

Once model 20 has been created, it can be used to estimate the property or properties of an unknown sample, as shown in FIG. 1b. In particular, the unknown sample 22 is analyzed using analytical instrument 16 (the same instrument shown in FIG. 1a), to produce measurement data that is input to model 20. The model produces an estimate of the property or properties of the unknown sample.

While the above-described multivariate calibration technique is very powerful, a significant limitation of the technique has recently been recognized. This limitation is based upon the fact that no two analytical instruments are precisely identical to one another, even instruments of the same type coming from the same manufacturer. Thus a calibration model determined using a first instrument cannot generally be used for other instruments of the same type, without a significant loss of accuracy. The ideal way to avoid this problem would be to calibrate each individual instrument, using all of the samples in the calibration set. However, complete recalibration of each instrument is impractical in many situations. Complete recalibration, for example, could often require the transportation of a large number of calibration samples to the site of each instrument, a challenging task when the samples are numerous, chemically or physically unstable, or hazardous. It would therefore be highly useful to develop techniques for transferring a calibration model derived for a first, reference instrument for use on a second, target instrument.

A closely related problem occurs when the responses measured on a single instrument change over a period of time for any reason, for example, temperature fluctuations, electronic drift, wavelength or detector instability, etc. If such changes occur after the development of a calibration model, then subsequent use of the model may produce erroneous results. Conceptually, the problem of differences between instruments is nearly identical to the problem of variation of a single instrument over time, although they are associated with different causes. Both problems involve calibration on a reference instrument, and an attempt to use the calibration model on a target instrument that produces responses that differ from those of the reference instrument in some way. The target instrument may be either the same instrument at a later time, or a different instrument.

It is in the area of NIR (near infrared) analysis of agricultural products that the most work in transferring calibration models has been accomplished. Osborne and Fearn (1983) investigated the effects of transferring single wavelength calibration models between nine different instruments for the prediction of protein and moisture in wheat flour, using NIRA spectroscopy. Single wavelength bias correction terms for the two calibration equations on each instrument were determined, and the long-term stability of the calibration was studied. Later, Shenk, Westerhaus and Templeton (1985) published results from a study where a large number of candidate calibration equations were developed on a single instrument for the prediction of several properties related to the forage quality of grasses, and then transferred to six other instruments. The "best" equation was adjusted for bias, offset and wavelength selection on the other instruments, and the standard error of prediction was compared between the original and the other instruments for a set of 60 common samples.

Recently, Mark and Workman (1988) published work describing the selection of wavelengths for NIR calibration, based upon their robustness toward wavelength shifts between instruments. Unfortunately, all of the above-described methods use only a single, or small number, of wavelengths, and are not generally applicable to a multivariate calibration. U.S. Pat. No. 4,866,644 describes a calibration method that attempts to correct for full spectral responses. However, the applicability of the technique described in this patent is limited by its univariate nature.

SUMMARY OF THE INVENTION

The present invention provides a technique for transferring a multivariate calibration model from a reference instrument to a target instrument. The target instrument may be a different instrument, or the same instrument at a later time. Using the invention, it is not necessary to determine the physical cause of the variation between instruments to perform the calibration transfer.

In a first preferred embodiment, referred to herein as "direct" calibration transfer, a plurality of transfer samples are selected, and a plurality of measurements are made of the transfer samples, using the reference instrument. This step produces a reference instrument response for each transfer sample. A plurality of measurements are made of the transfer samples using the target instrument, to produce a target instrument response for each transfer sample. Finally, transfer coefficients are produced that are capable of performing a multivariate estimation of the reference instrument responses for the transfer samples from the target instrument responses for the transfer samples.

Once the transfer coefficients have been produced, they may be used to estimate a property of an unknown sample. To produce such an estimate, the property in question is measured for each of a plurality of calibration samples, to produce property data. For each calibration sample, a plurality of measurements are made using the reference instrument, to produce a reference instrument response. The property data is then combined with the reference instrument responses for the calibration samples, to produce a multivariate prediction model for the reference instrument. The target instrument is used to produce a target instrument response for the unknown sample, and the transfer coefficients are then used to convert this target instrument response into an estimate of the reference instrument response for the unknown sample. The estimated reference instrument response is then combined with the multivariate prediction model for the reference instrument, to predict the property for the unknown sample.

In an important variation of the direct embodiment, referred to as the piecewise technique, the transfer coefficients comprise a plurality of estimation coefficients for estimating each reference data value from more than one but less than all of the target data values. The piecewise technique produces a significant improvement over the direct technique, particularly with a small number of transfer samples.

In a further preferred environment, referred to as "classical" calibration transfer, a property is measured for each of a plurality of calibration samples to produce property data. For each sample, a plurality of measurements are also made using the reference instrument, to produce a reference instrument response for each sample. For each transfer sample in a subset, a plurality of measurements are made using the target instrument, to produce a target instrument response. The reference instrument responses for the calibration samples, the target instrument responses for the transfer samples, and the property data are then combined to produce an estimate of the responses of the target instrument to the calibration samples. These estimates are then combined with the property data to produce a multivariate prediction model for the target instrument. In a further embodiment, referred to as "inverse" calibration transfer, a multivariate prediction model for the reference instrument is produced using the reference instrument responses for the calibration samples and the property data. This multivariate prediction model is then combined with the reference and target instrument responses for the transfer samples, and the property data, to produce a multivariate prediction model for the target instrument. For both "classical" and "inverse" techniques, the target instrument model can subsequently be used to predict the property in question of an unknown sample.

BRIEF DESCRIPTION OF THE DRAWINGS

FIGS. 1a and 1b generally illustrate the process of constructing a multivariate model from a set of calibration samples, and using the model to predict the properties of an unknown sample;

FIGS. 2a and 2b illustrate the prediction process using the classical calibration transfer technique of the present invention;

FIGS. 5a and 5b graphically illustrate the piecewise technique;

DETAILED DESCRIPTION OF THE INVENTION

Figure 3A:
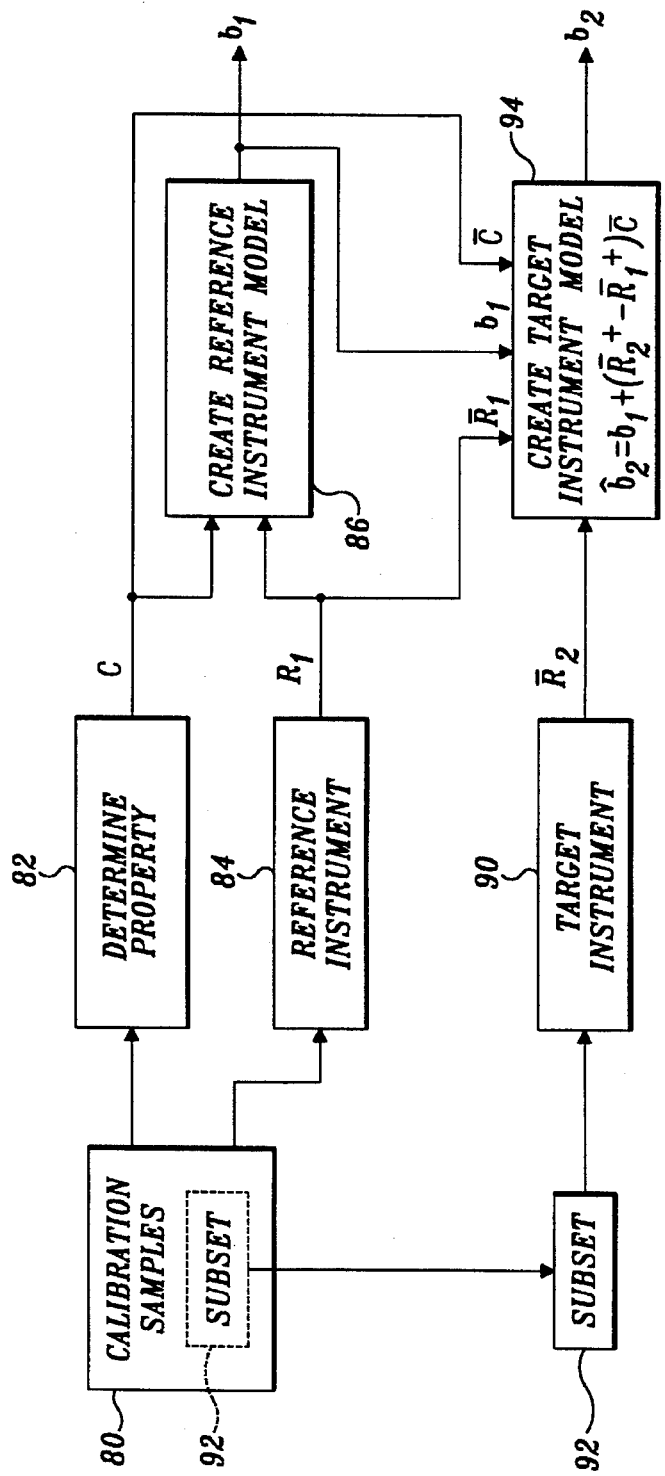
FIGS. 3a and 3b illustrate the prediction process using the inverse calibration transfer technique of the present invention.

To make the following discussion less abstract, it will initially be assumed that the analytical instrument is a spectrophotometer that measures the absorption of light by a sample at each of a plurality of wavelengths, and the set of measurements or instrument responses will be called a spectrum. Spectroscopy examples include near infrared, Fourier transform infrared, ultraviolet-visible, infrared emission and fluorescence. However, the invention is not limited to spectroscopy, and can be applied to any instrument or collection of instruments that provides multiple measurements per sample.

To calibrate the analytical instrument, the spectra of a group of calibration samples are measured. The properties of interest are known in advance for the calibration samples, or are measured by a suitable reference method. A multivariate calibration model is then built that relates the spectra of the samples to the properties for the samples. The multivariate calibration model may be built using singular value decomposition, principal component regression, partial least squares, or other known regression or multivariate modeling or prediction techniques. Finally, the spectrum of an unknown sample is measured, and the property for the unknown sample is estimated from the model. The properties to be estimated may be chemical properties such as the concentrations of one or more analytes, the protein content of wheat, etc., or other properties such as the octane number of gasoline samples.

It may initially be assumed that there is a linear relationship between spectra and the concentration of the analytes in a given sample. Thus, the response of the instrument (i.e., the absorbence) at a given wavelength i, designated $r_i$, can be written $$r_i = \sum_j c_j k_{ji} + e \tag{2}$$

where the summation is over the number of analytes in the sample. Equation (2) is an expression of the Lambert-Beer law and linear additivity, the former simply states that the absorbence $r_i$ at a given wavelength i is the sum of the absorbences of the individual analytes at that wavelength, and the latter that the absorbence of each analyte j is equal to the product of the intrinsic absorbence of pure analyte j at wavelength $i(k_{ji})$, times the concentration of analyte $j(c_j)$. The quantity e represents the model error.

Equation (2) can be rewritten as a vector equation as follows:

$$r = \sum_j c_j k_j \tag{3}$$

where r (without subscript) is a vector whose components are the absorbence of the sample over the different measurement wavelengths, i.e., r is the spectrum of the sample. $k_j$ (single subscript) is a vector that represents the spectrum of pure analyte j. The error term has been omitted from Equation (3). Thus, Equation (3) simply states that the spectrum of the sample is the sum of the individual analyte spectra weighted by the analyte concentrations.

Assume now that a set of calibration samples (i.e., a calibration set) has been prepared, and that the spectrum of each member of the calibration set has been measured. The spectra can be formed into a matrix R, where each row of R is the spectrum r of one of the calibration samples. Thus matrix R has the dimensions of number of samples by number of wavelengths. Generalizing Equation (3) to the ease of multiple samples, the matrix R can therefore be expressed as follows $$R = CK \tag{4}$$

Matrix C is a concentration matrix each of whose rows are the analyte concentrations in a given sample. Thus matrix C has dimensions of samples by analytes. Matrix K is dimensioned analytes by wavelengths. Referring to FIGS. 1a and 1b, matrix R represents the measurement data produced by the analytical instrument, matrix C represents the independently determined properties of the samples (here analyte concentrations), and matrix K represents the sensitivity for all analytes, which can be solved from Equation (4).

$$K = C^+ R \tag{5}$$

where $C^+$ is the pseudoinverse of C. One then makes up the calibration set consisting of samples having known concentrations of the analytes present in the samples. Thus for this calibration set, the matrix C is known. One then measures the spectra of the calibration samples, thereby determining matrix R. Equation (5) is then used to determine matrix K for this calibration set. Thereafter, the response or spectrum r of an unknown sample is measured, and multiplied by the inverse of K, to calculate the concentrate of analytes in the unknown sample.

Imagine now that the above steps have been performed on a first, reference instrument, and let $K_1$ be the matrix K as determined using the first, reference instrument. However it is now required to use this calibration model on a second, target instrument. For the target instrument, an equation similar to Equation (4) may be written as follows:

$$R_2 = CK_2 = C(K_1 + \Delta K) \quad (6)$$

where $K_2$ is the model to be determined for the target instrument, and $\Delta K$ is the difference matrix $K_2 - K_1$. Imagine now that a subset of the calibration samples is selected, and that the response of the target instrument is measured using the samples in the subset. The samples in the subset are referred to herein as the "transfer" samples. Using a bar to denote the samples in the subset, the above $$\bar{R}_1 = \bar{C} K_1 \quad (7)$$

$$\bar{R}_2 = \bar{C} K_2 = \bar{C}(K_1 + \Delta K) \quad (8)$$

Equations (7) and (8) may be solved for $\Delta K$ as follows $$\Delta K = \bar{C}^+ (\bar{R}_2 - \bar{R}_1) \quad (9)$$

Substituting $\Delta K$ in Equation (6), and using Equation (4), $R_2$ may be estimated as follows $$\hat{R}_2 = R_1 + C \bar{C}^+ (\bar{R}_2 - \bar{R}_1) \quad (10)$$

With $\hat{R}_2$ and C, a new calibration model can, be built for the target instrument (as per Equation (5)), using standard multivariate calibration methods.

Because Equation (4) is often referred to as the "classical" calibration model, the calibration transfer technique described above will be referred to herein as classical calibration transfer. The process of classical calibration transfer according to the present invention is summarized in FIGS. 2a and 2b. One begins with the preparation of a set of calibration samples 40. The concentrations of the different analytes in each member of the calibration set are then determined in step 42. Often the concentrations will be known because they are simply recorded at the time that the samples are prepared. Each sample in the calibration set is then analyzed by reference instrument 44 to produce the data comprising matrix $R_1$. In step 46, the property data C is combined with measurement data $R_1$ to produce a calibration model $B_1$ for the reference instrument. To transfer model $B_1$ to target instrument 50, a subset 52 of the calibration samples is transported to the site of the target instrument, and analyzed by the target instrument to produce $\bar{R}_2$, i.e., the spectra of the transfer samples in the subset, as measured on the target instrument. In step 54, the target instrument spectra for the full set of calibration samples $R_2$ are estimated, per Equation (10) above. Then in step 56, target instrument model $B_2$ is created by combining $\hat{R}_2$ and C, again by using standard multivariate calibration methods. Thereafter, as shown in FIG. 2b, when unknown sample 60 is analyzed using target instrument 50, the resulting spectra $r_2$ is input to model $B_2$, to produce an estimate of the properties of the unknown sample. Although very powerful, the classical calibration transfer technique does suffer from one significant limitation, i.e., it assumes that the concentrations for all analytes contributing to the response must be known. In a case in which it will not be possible to determine the concentrations of all of the analytes present in the samples, a so-called inverse calibration model may be developed from the equation $$c_j = \sum_i R_{ji} b_i \quad (11)$$

where the summation is now over the number of wavelengths measured by the analytical instruments, $c_j$ is the concentration or other property measured for sample j, $R_{ji}$ is the absorbence or instrument response for sample j at wavelength i, and $b_i$ is the regression coefficient at the same wavelength i. Equation (11) can be generalized as follows $$c = Rb \quad (12)$$

where c is a column vector having one element for each sample, R is a matrix having dimensions of samples by wavelengths, and b is a column vector of regression coefficients, one coefficient for each wavelength.

Using inverse calibration techniques, one measures the spectrum for each sample in the calibration set to determine matrix R, determines the properties c for the samples in the calibration set using a standard, accepted technique, and then inverts R in Equation (12) to determine the regression coefficients b. Therefore, with reference to FIGS. 1a and 1b, the matrix R once again represents the measurement data produced by the analytical instrument, and vector e represents the property data determined for the samples in the calibration set. For the inverse technique, it is not necessary to know the concentrations of all the various analytes making up the calibration samples, but only the analytes of interest.

In order to provide calibration transfer for inverse calibration models, one may rewrite Equation (12) as follows, where as above, subscripts 1 and 2 refer to reference and target instruments respectively.

$$c = R_1 b_1 \quad (13)$$

$$c = R_2 b_2 = R_2 (b_1 + \Delta b) \quad (14)$$

The procedure begins by measuring property c for the full set of calibration samples, and measuring the response of the reference instrument for all samples, to produce measurement data $R_1$. From c and $R_1$, the inverse calibration model for the reference instrument $b_1$ may be determined. One then selects a subset of the calibration samples, and determines the measurement data for these transfer samples on the target instrument. If, as above, the quantities relating to the transfer samples are denoted with a bar, one may write $$\bar{c} = \bar{R}_1 b_1 \quad (15)$$

$$\bar{c} = \bar{R}_2 b_2 = \bar{R}_2 (b_1 + \Delta b) \quad (16)$$

Combining Equations (15) and (16) and using Equation (14), a standardized regression vector for the target instrument $b_2$ can be estimated as follows:

$$\hat{b}_2 = b_1 + (\hat{b}_2 - b_1) = b_1 + (\bar{R}_2^+ - \bar{R}_1^+) \bar{c} \quad (17)$$

This method can be expanded to work with more than one property at a time, by making the c vector into a matrix, and using a matrix of regression vectors. With the inverse method, only the concentration of the analyte of interest needs to be known.

Figure 3B:
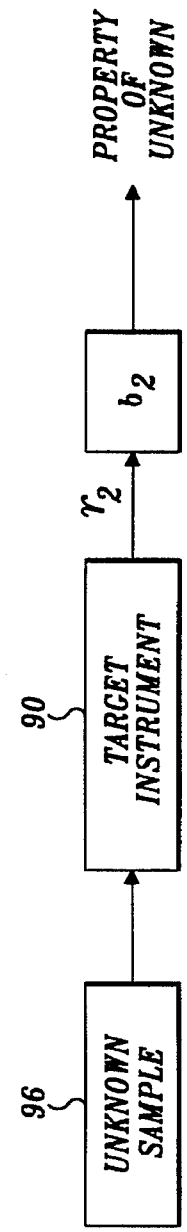

Inverse calibration transfer according to the present invention is summarized in FIGS. 3a and 3b. One begins again with the preparation of a calibration set 80 of standard samples. The property or properties of interest of each standard sample are then determined in step 82, to produce property data c. The calibration samples 80 are then analyzed by reference analytical instrument 84 to produce the resulting spectra $R_1$. The c and $R_1$ data may then be mathematically combined in step 86 to create model $b_1$ that may be used to predict the properties of unknown samples using the reference instrument.

To transfer the calibration represented by model $b_1$ to target instrument 90, a subset 92 of calibration samples 80 is selected, and these transfer samples are transported to and analyzed by the target instrument, to produce spectra $\bar{R}_2$.

The target instrument model $b_2$ is then estimated in step 94, using Equation (17). Thereafter, unknown sample 96 is analyzed by target instrument 90 to produce spectrum $r_2$, which may then be combined with model $b_2$ to estimate the property of the unknown sample.

With the inverse model according to the present invention, the regression coefficients determined from the full calibration set on the reference instrument are corrected by making use of the differences in the inverted responses of the reference and target instruments to a subset of the samples. Thus, in contrast to classical calibration transfer, one does not correct all of the spectra measured on the reference instrument. One begins instead from the actual regression coefficients calculated on the reference instrument, and applies a correction term to those regression coefficients. Once the corrected regression coefficients are determined, they may then be combined with the measured spectrum on the target instrument to determine the property of an unknown sample.

A third preferred embodiment of the invention makes use of what will be termed herein "direct" calibration transfer between the reference and target instruments. This technique begins by postulating the existence of a transfer matrix F that is capable of transforming responses measured for transfer samples on the target instrument into the responses that would have been measured for the same samples by the reference instrument. In particular, the transformation matrix is defined as follows $$\bar{R}_1 = \bar{R}_2 F \qquad (18)$$

Thus F is a square matrix, dimensioned wavelengths by wavelengths, and can be calculated directly as follows $$F = \bar{R}_2^+ \bar{R}_1 \qquad (19)$$

To make use of the transfer matrix, the response $r_1$ of an unknown sample measured on the reference instrument is estimated from the response of that sample on the target instrument $r_2$ as follows $$\hat{r}_1^T = r_2^T F \qquad (20)$$

where the superscript, T, refers to the transpose of a vector or matrix. Once $\hat{r}_1$ is estimated using Equation (20), the model developed on the reference instrument can be used directly for the prediction of the property or properties of the unknown sample.

Figure 4A:
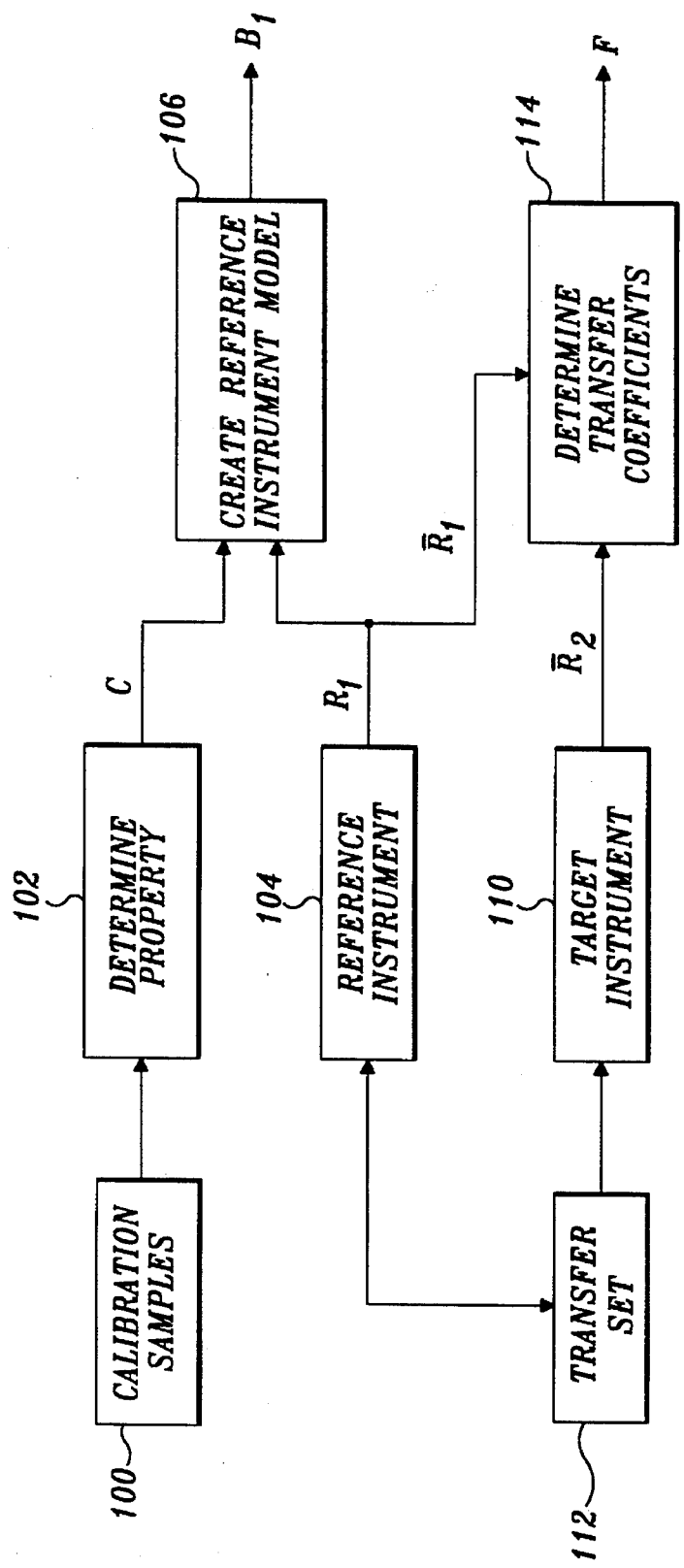
FIGS. 4a and 4b illustrate the prediction process using the direct and piecewise calibration transfer techniques of the present invention.
Figure 4B:
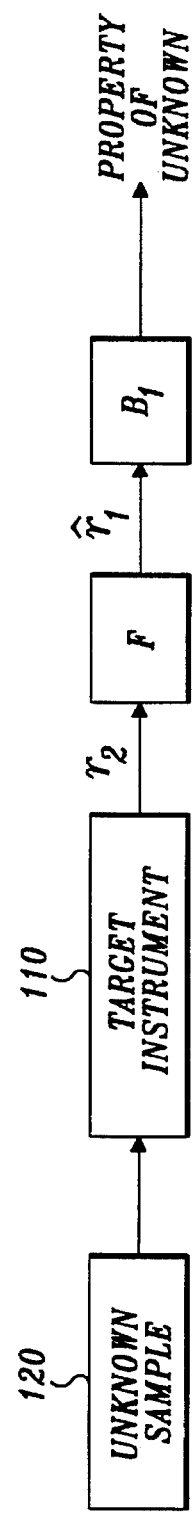

Direct calibration transfer in accordance with the present invention is summarized in FIGS. 4a and 4b. Again, one begins with standard samples 100 that are analyzed in step 102 to determine one or more properties represented by C. The standard samples may then be analyzed using reference analytical instrument 104 to produce measurement data $R_1$, and property data C may then be combined with measurement data $R_1$ in step 106 to produce model $B_1$. Thereafter, model $B_1$ may be used to predict properties of unknown samples using the reference analytical instrument.

To transfer this calibration to target instrument 110, a subset 112 of the standard samples is selected, and these transfer samples are analyzed using the target instrument, to produce data $\bar{R}_2$. This data is then mathematically combined in step 114 with the corresponding spectra for the transfer samples as measured on the reference instrument $\bar{R}_1$, to determine transfer matrix F. Thereafter, to analyze unknown 120 on target instrument 110, the response $r_2$ of the target instrument is combined with matrix F, as shown in Equation (20), to produce an estimate of the corresponding response $r_1$ that would have been measured for the unknown on the reference instrument. Response $r_1$ may then be input to model $B_1$ that has been determined for the reference instrument, to produce an estimate of the property of the unknown sample.

In direct calibration transfer, the F matrix may often be calculated from a relatively small subset, and Equation (19) is often undetermined with respect to F. To obtain a determined F matrix, singular value decomposition may be used to reduce the original response matrix to the size of (i.e., to the number of transfer samples in) the subset 112 used for calibration transfer. In this technique, $R_1$, $\bar{R}_1$, $\bar{R}_2$ and $r_2$ are preferably projected onto the column space of $R_1$. The scores obtained by projection are then used in place of the original response matrices. For example, for a system of rank 3, a 5-sample subset might be used for the calibration transfer, and a rank 5 column space of $R_1$ would comprise the first five right singular vectors from the singular value composition of $R_1$. Note that it is not necessary to truncate this projection down to the actual rank of the system. In fact, by selecting a number of subset samples larger than the actual rank of the system and projecting down to that rank one solves the undetermined problem and has extra rank to account for non-linear differences between instruments. Since the noise contained in the data could also be discarded in this manner, the same data preprocessing procedure may also be applied to the classical and inverse calibration transfer techniques, as well as to the piecewise technique described below.

In the three calibration transfer techniques described above, the number of transfer samples should be at least equal to the rank of $R_1$, in order to obtain an adequate calibration transfer. This requirement could prove difficult in many practical situations. Furthermore, it may be noted that in the direct standardization technique, the entire spectrum on the target instrument is used to fit each spectral point on the primary instrument. This can be seen by noting that Equation (18) can be written $$(\bar{r}_1)_{s,j} = \sum_{i=1}^{M} (\bar{r}_2)_{s,i} f_{i,j} \qquad (21)$$

Equation (21) states that the response $\bar{r}_1$ of the reference instrument, for sample s and wavelength j, is a linear combination of the target instrument responses $\bar{r}_2$ for the same sample, over all M wavelengths, weighted by the elements $f_{i,j}$ of the transfer matrix F. However for most real data, the response of the reference instrument at a given wavelength is a function of the responses of the target instrument only over a limited range of nearby wavelengths. This consideration leads to a fourth preferred embodiment of the invention, referred to as "piecewise" calibration transfer, that may be regarded as a subset of the direct technique. The piecewise technique is diagrammed in FIGS. 5A and 5B. FIG. 5A illustrates reference instrument response curves 130, as a function of wavelength, for five transfer samples. Although curves 130 are illustrated as essentially continuous functions, it will be appreciated that each curve in fact consists of a series of discrete samples along the wavelength axis. Brackets 132 represent the five measurements (one for each of five transfer samples) made at wavelength i. These points can be symbolized by $\bar{r}_1(i)$ it being understood that $\bar{r}_1(1)$ is a vector containing one element per transfer sample, FIG. 5B illustrates target instrument response curves 134 for the same five transfer samples. In the direct calibration transfer method described above, vector $\bar{r}_1(i)$ is modeled by all of the data shown in FIG. 5B. However, in the piecewise technique, the vector $\bar{r}_1(i)$ is modeled by the data in a window or range of the target instrument measurements, the window being symbolized by brackets 136 in FIG. 5B. In particular, for subset measurement $\bar{r}_1(i)$ at wavelength index i on the reference instrument, subset measurements on the target instrument $r_2(i-j), r_2(i-j+1), \ldots, r_2(i+k-1)$ and $r_2(i+k)$ at nearby wavelengths (from wavelength index i–j to wavelength i+k) are selected and put into a matrix $$X_i = [r_2(i-j), r_2(i-j+1), \ldots, r_2(i+k-1), r_2(i+k)] \quad (22)$$

For a nominal shift and linear intensity change from the reference to target instrument, $$r_1(i) \alpha r_2(n) \quad (23)$$

where n lies somewhere in the range i–j through i+k. However, in the more realistic case of non-nominal shift and nonlinear intensity change, Equation (23) will not hold. However in the piecewise technique, a multivariate regression of the form $$r_1(i) = X_i b_i \quad (24)$$

is used to perform the interpolation, and provide a reasonable approximation to the nonlinear intensity change. It is the fact that the rank of $X_i$ is less than or equal to the rank of $R_1$ that makes it possible to reduce the number of transfer samples. The regression vector $b_i$ may be calculated by various calibration methods, such as principal component regression or partial least squares. Once the regression vectors have been determined using the transfer samples, the model is used piece-by-piece to transfer the spectrum of an unknown measured on the target instrument into the corresponding spectrum that would have been measured on the reference instrument, as illustrated generally in FIG. 4B. For each end on the reference instrument spectrum, a window of a predetermined size cannot be constructed, and both ends may simply be discarded. Alternately, extrapolation may be used on each end using a portion of the window.

To improve the modeling of nonlinear intensity change between the reference and target instruments, nonlinear terms, e.g., quadratic terms, may be added to matrix $X_i$ in Equations (22) and (24). For example, a term such as $r_2(i)^2$ may be added. The effect of this extension of the model is discussed below in connection with the simulation results.

When compared to direct standardization, piecewise standardization is in fact a calculation of transfer matrix F by setting most of the off-diagonal elements to zero, i.e., $$F = \text{diag}(b_1^T, b_2^T, \ldots, b_M^T) \quad (25)$$

where M is the number of wavelengths in the spectra. If there is only a linear intensity change and no wavelength shift, then F will be a diagonal matrix. If there are both linear intensity change and +1 unit wavelength shift, for example due to misalignment of a monochromator, then F will be a matrix with nonzero elements on the subdiagonal and zeros elsewhere. For the more general case, where intensity change is nonlinear and shift varies with wavelength, (e.g., peak broadening), F will be a matrix with nonzero elements in a window along the main diagonal, and zeros elsewhere.

For all of the above-described techniques, the subset used for calibration transfer must contain enough information to describe the differences between the reference and target instruments. A stepwise procedure may be employed to select the calibration samples with the highest leverage, assuming that there are no outlines in the calibration set. The information contained in each selected calibration sample is removed from the remainder of the samples by a linear transformation, so that they are all orthogonal to the sample selected. This procedure continues until the desired number of transfer samples have been selected. In particular, selection of transfer samples can proceed first by calculating the hat matrix of the full calibration set as follows $$H = R_1 R_1^+ \quad (26)$$

The sample with the highest leverage (maximum $h_{ii}$) is selected, and the selected row $r_i$ is orthogonalized against every other row (sample) to obtain a new $R_1$ by means of the linear transformation $$r_j' = \alpha r_i + \beta r_j \quad (j \text{ not equal to } i) \quad (27)$$

where the prime is used to differentiate the $r'_{js}$ before and after the transformation, by using the orthogonal condition $$r_j' \cdot r_i = 0 \quad (28)$$

One then checks to see if enough transfer samples have been selected. If not, one returns to Equation (26) using matrix $R_1$ with the appropriate row removed, and the remainder of the rows transformed, and repeats the above-described procedure.

Figure 6:
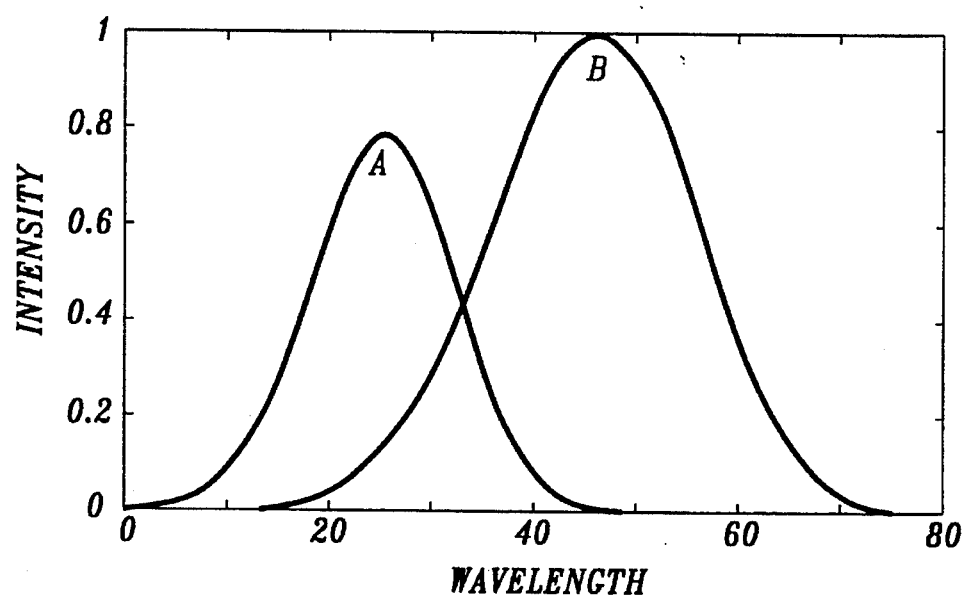
FIG. 6 illustrates the spectra of two hypothetical analytes used for a simulation study.
Figure 7:
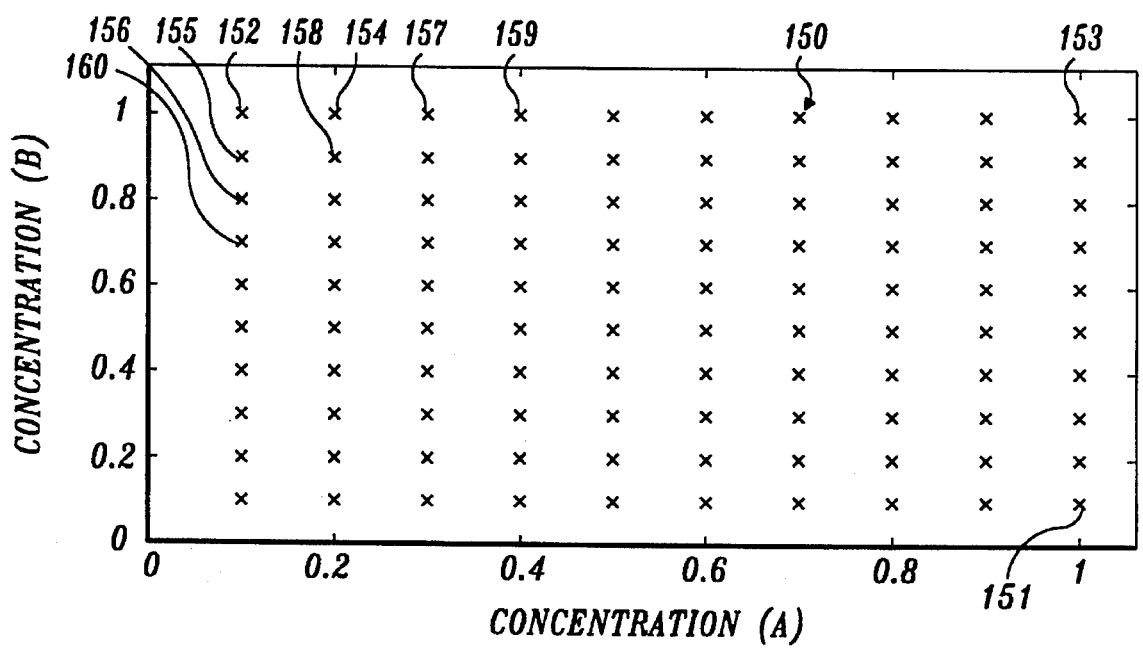
FIG. 7 illustrates the concentrations of the analytes in the calibration samples, as well as the selection of subset samples.

To test and compare the effects of various factors on the results obtained by the calibration transfer techniques of the present invention, computer simulation was employed with a two-analyte system. Two pure spectra were simulated from Gaussian peaks at 80 wavelength points, as shown by curves A and B in FIG. 6. A 100-sample calibration set was created from these two components by letting the concentration of each component vary from 0.1 to 1.0 in steps of 0.1. The compositions of the 100 samples are illustrated by points 150 in FIG. 7. Thus, for this simulation, the matrix of pure spectra K is dimensioned 2×80 (analytes by wavelengths), and the concentration matrix C is dimensioned 100×2 (samples by analytes). The linear response data for the reference instrument $R_1$ is then formed using the relationship:

$$R_1 = CK \quad (29)$$

To simulate a deviation from the Lambert-Beer law, $R_1$ was modified by subtracting a 30% quadratic term from each element and by adding 1% random noise. By cross-validation, it was determined that the optimal rank for prediction using partial least squares was 5, with standard errors of prediction (SEP) for analytes A and B of 0.0055 and 0.0038, respectively.

For the target instrument, a 20% linear increase in response was added, to simulate a linear gain difference on the target instrument. A subtraction of a 10% quadratic term was then applied, to generate a nonlinear response variation. A nonlinear wavelength shift was simulated using a quadratic function, the parameters of which were determined such that the shift at both ends of each spectrum was +2 wavelength points, and the shift at the extrema of the quadratic function was –2 points. The spectra were subjected to this nonlinear wavelength shift via linear interpolation, and 1% noise was added, to finally produce the full calibration set on the target instrument, $R_2$. Cross-validation indicated that the optimal rank remained 5, with approximately unchanged SEPs for both analytes.

Figure 8:
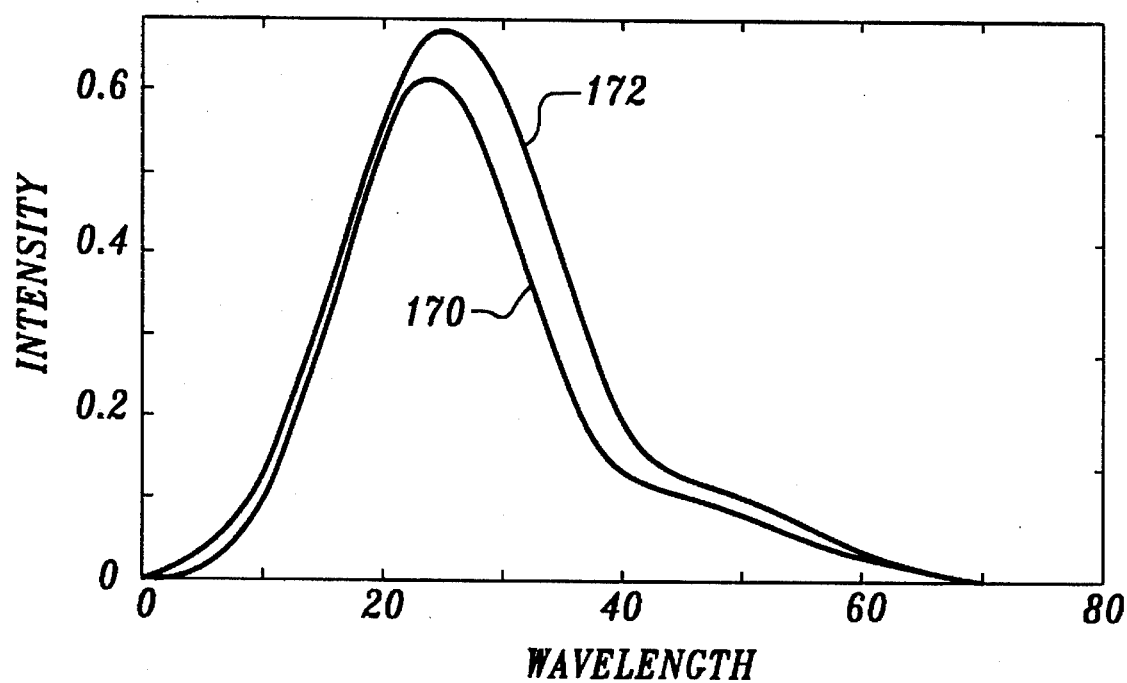
FIG. 8 illustrates the difference between the reference and target instrument spectra for one of the subset samples.

The basic idea behind calibration transfer is to select a subset $\bar{R}_1$ composed of only a few transfer samples from $R_1$, and remeasure these transfer samples on the target instrument to produce $\bar{R}_2$. Using the technique described above for transfer sample selection, the first ten samples, arranged in order of decreasing leverage, are indicated by reference numerals 151–160 in FIG. 7. Not surprisingly, the three highest leverage samples (151–153) occur at extremes of concentration of at least one analyte. In FIG. 8, the response (spectrum) of sample 151 on the reference instrument is shown by curve 170, while curve 172 shows the response of this sample on the target instrument. It may be seen that there is significant variation between the two instruments in this simulation.

In addition to the calibration technique provided by the present invention, there are other options available when the problem of response variation from one instrument to another occurs. For example, one can combine $R_1$ and $\bar{R}_2$ together to produce a single model. Another option is to make the new calibration based only on $\bar{R}_2$ (herein called subset recalibration). The former approach is found to cause very large degradation for prediction on the target instrument, and thus only the latter was included in this simulation for comparison purposes. In the simulation, the subset size was changed from 3 to 10, in order to study its effect on the SEP. To increase accuracy, each simulation was repeated 250 times, and the results averaged.

Figure 9:
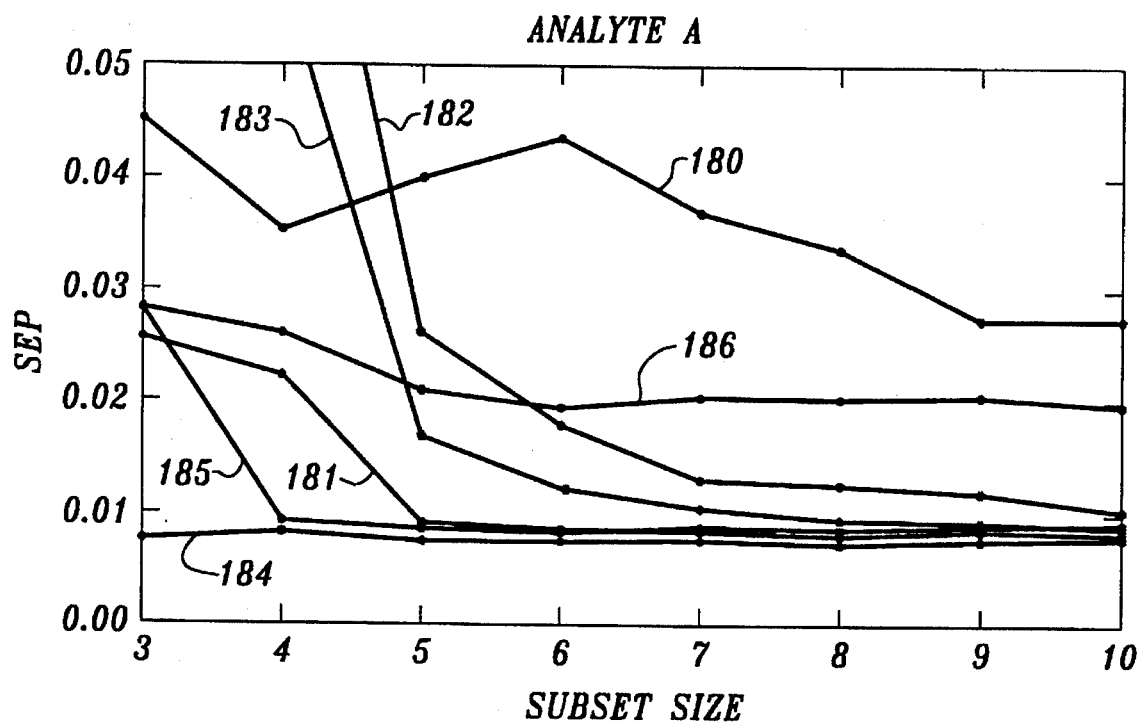
FIG. 9 graphs the standard error of prediction (SEP) versus subset size for analyte A for different transfer techniques.

The results of the simulation are set forth in FIG. 9 for analyte A, by means of graphs showing the standard error of prediction (SEP) as a function of subset size. Curve 180 shows the results of the prior art technique of subset recalibration. Curves 181, 182, 183 and 184 show the results of the classical, inverse, direct and piecewise techniques, respectively, according to the present invention. Curve 185 shows the results of using the piecewise technique with a quadratic term added to matrix $X_i$. Finally, curve 186 represents the results of another prior art technique set forth in U.S. Pat. No. 4,866,644 (Shenk).

It can be seen that all calibration transfer techniques do significantly better than subset recalibration (180), demonstrating that the calibration information in $R_1$ is indeed being transferred. Both the direct and the inverse techniques give large errors (out of the FIGURE) when the number of transfer samples is smaller than 5, which is the rank of $R_1$. However, as the number of transfer samples increases from 5, the prediction accuracy is consistently improved, indicating that both methods have an intrinsic ability to handle response variations, but that a larger number of transfer samples is preferred for better noise filtering. Between these two methods, direct outperforms inverse, which is believed to be due to the unfavorable error propagation in the calculation of $\Delta b = \bar{b}_2 - \bar{b}_1$ (Equation (17)).

The classical technique works better than either direct or inverse, and works even when the subset size is smaller than the rank of $R_1$. Although the Shenk method (186) performs better than subset calibration, it is not able to attain the accuracy of the other approaches. The Shenk technique does not put any explicit requirement on the subset size, and therefore also works when the number of transfer samples is smaller than 5. However, the prediction accuracy is not significantly improved when more transfer samples are added, indicating a lack of intrinsic modeling ability.

Of all the methods tested, the piecewise technique gives the best results. Significantly, a very small SEP is reached with only 3 transfer samples. It was expected that the piecewise with the quadratic term would perform better, since the response variation simulated was quadratic. However, this was not the case, especially when the subset size was small. The reason for this variation may be overfitting with the quadratic piecewise model. Like many multivariate calibration models, piecewise standardization does not need a nonlinear term to sufficiently account for a nonlinear response change.

Figure 10:
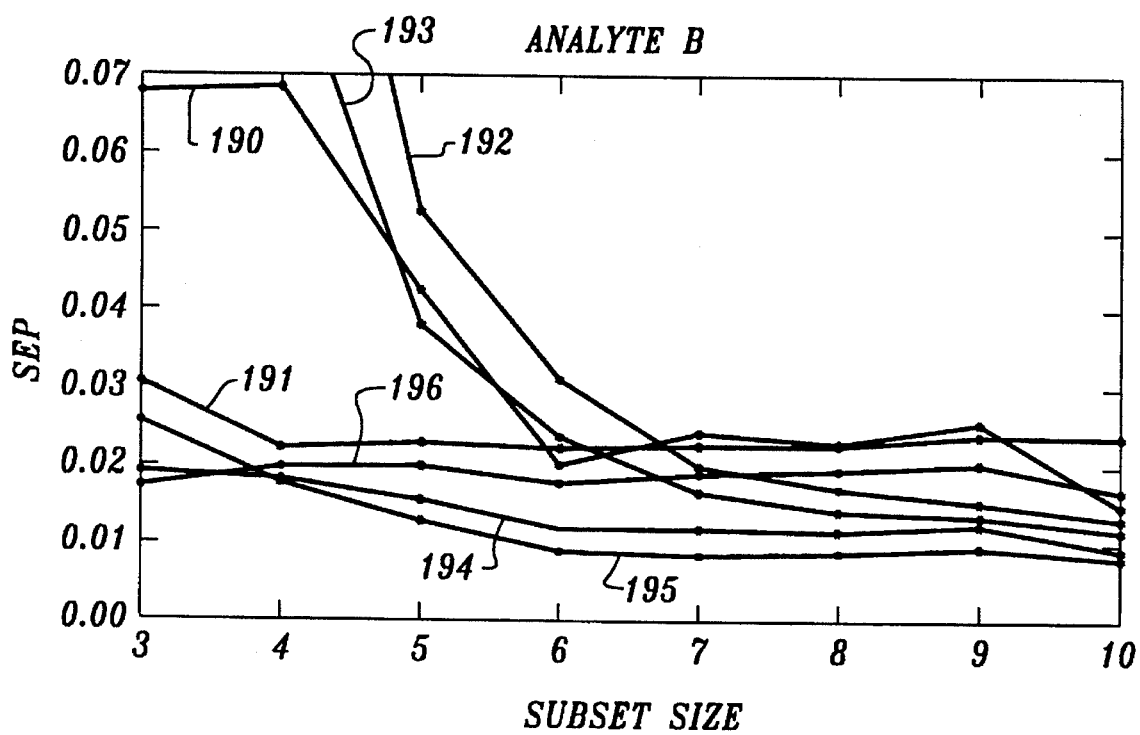
FIG. 10 graphs SEP versus subset size for analyte B for the same techniques.

FIG. 10 graphs SEP versus subset size for analyte B, with curves 190–196 corresponding to curves 180–186 in FIG. 9. The direct technique still outperforms the inverse technique, but both methods cannot give better results than subset recalibration until the subset size reaches 7. From its pure spectrum (FIG. 6), it is noted, that analyte B has a higher sensitivity. In the simulation of nonlinear response change, the signal at each wavelength, after a 20% linear gain, is reduced by 10% of its quadratic form, to generate the response on the target instrument. Thus, in the spectral region where the signal for analyte B dominates, a larger nonlinearity is involved. The results shown in FIG. 10 indicate that more transfer samples will be needed for both methods to obtain a sufficient correction for this larger nonlinearity.

Still referring to FIG. 10, while the direct and inverse techniques again produce large errors when the subset size is smaller than 5, the classical model still provides a reasonable approximation, and outperforms subset recalibration. However, when the subset size increases to 6, the results are similar to that of subset recalibration, demonstrating an intrinsic limitation of its modeling ability for nonlinear data. For analyte B, the Shenk method does better than the classical technique, due possibly to a better handling of the wavelength shift, since the nonlinear shift simulated has its extrema at near the center of the spectrum, which is also near the peak of analyte B. Again, a lack of fit becomes obvious when the subset size increases, which is consistent with the results obtained by analyte A.

The piecewise approach again outperforms all other methods in all but one case, where the Shenk method gives slightly better results with three transfer samples. This is related to the window size, and is further discussed below. The piecewise technique with a quadratic term, however, does slightly better than piecewise without the quadratic term, except for the case of three transfer samples, where overfitting is believed to occur. As already described, the nonlinear response change associated with analyte B is larger; therefore, an explicit modeling does help somewhat at the risk of overfitting.

Figure 11:
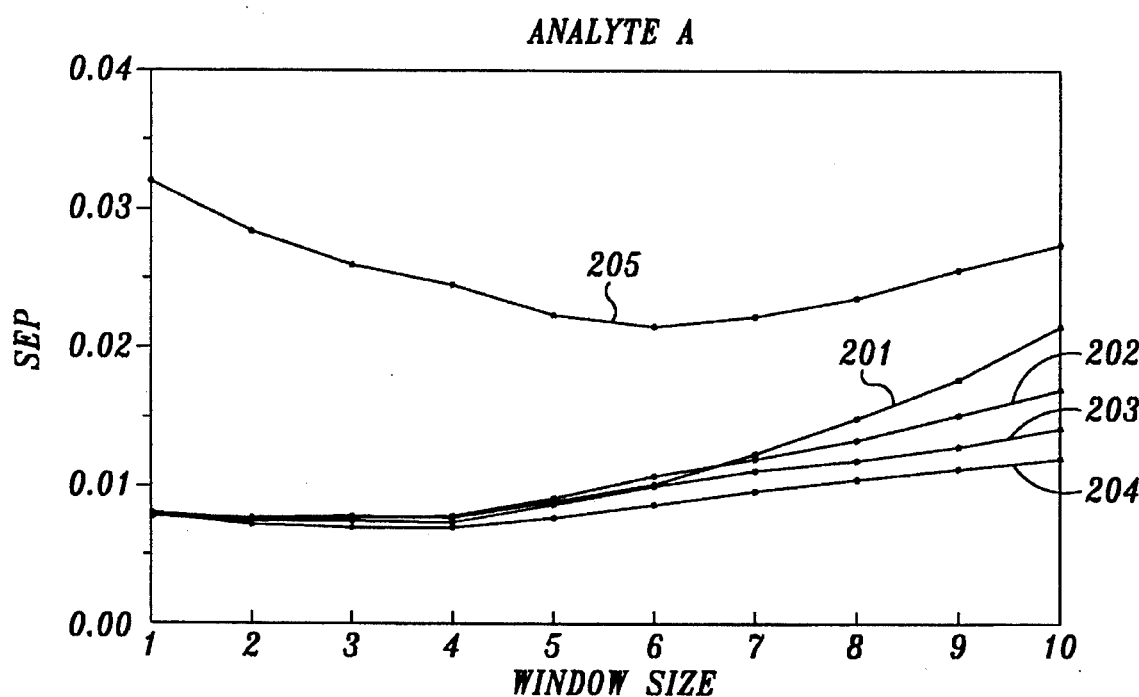
FIG. 11 graphs SEP for analyte A versus window size for the piecewise method.

In the above simulations, for the piecewise technique, a shift is known to lie between +2 and −2 wavelength points, and the window parameters j and k in Equation (22) are both set equal to 2. Because this might not be appropriate when nonlinear response variation is involved, the simulation was again run varying the window size, and the results are indicated in FIGS. 11 (analyte A) and FIG. 12 (analyte B). Referring initially to FIG. 11, curve 201 represents the variation of SEP with window size for a subset of 3, and curves 202–204 show their results for subsets of 5, 7 and 9, respectively. For comparison, curve 205 shows the Shenk technique with a subset of 3. It can be seen that the piecewise technique works well for j=k=1 to j=k=4, and that the increase of subset size does not have a significant influence on the results. This indicates that an effective correction has been obtained with this method. When the window size increases to about 4, the inclusion of additional transfer samples begins to have a negative effect on the results, suggesting the occurrence of overfitting when too many nonrelevant channels are included. This is the main problem with direct standardization when the full spectral region is included.

Figure 12:
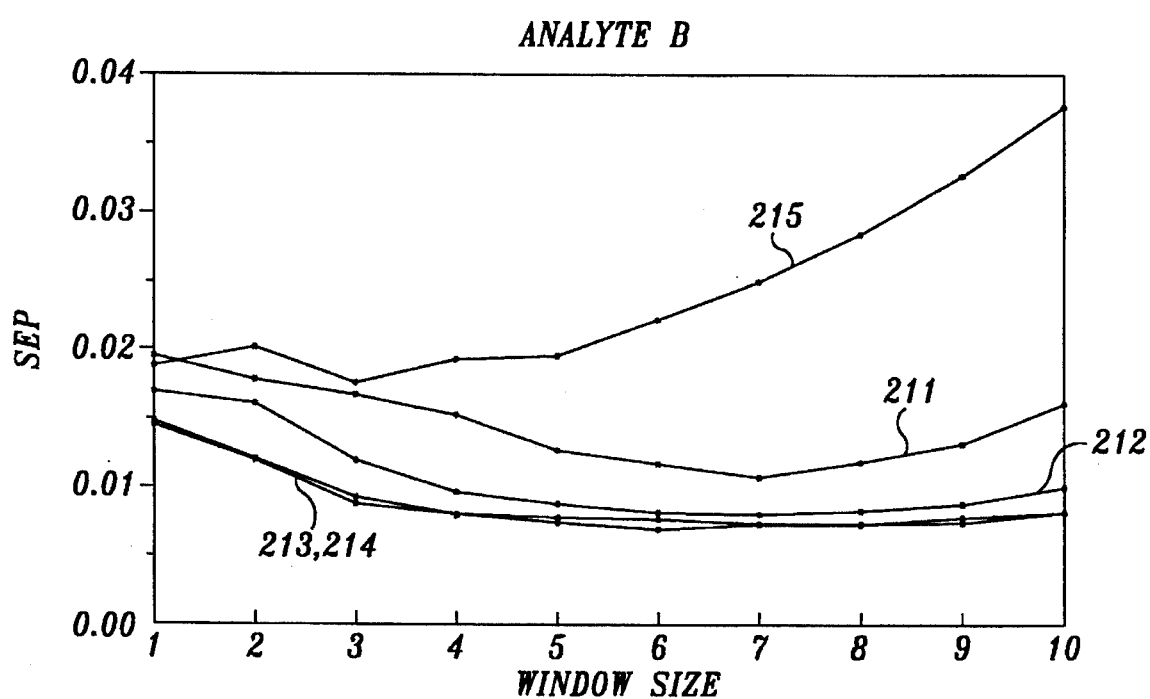
FIG. 12 graphs SEP for analyte B versus window size.

Referring to FIG. 12, it can be seen that the optimal window size for analyte B is about 7, substantially larger than for analyte A, confirming that a larger nonlinear response change is associated with this analyte. The standard errors of prediction for analytes A and B, at their optimal window sizes with 5 subset samples, were 0.0077 and 0.0065, respectively. Compared to the full set cross-validation SEPs of 0.0055 and 0.0038, this accuracy is quite satisfactory, since only 5 subset samples need to be remeasured on the target instrument.

While the preferred embodiments of the invention have been illustrated and described, variations will be apparent to those skilled in the art. For example, it often occurs that the samples to be analyzed form two or more distinguishable groups, such as matte samples versus clear samples, or samples from different production runs. In such a case, a single instrument (at a single time) may measure different responses for matte versus clear samples, even though the two samples have identical properties, e.g., identical concentrations of analytes, octane numbers, etc. In the cases previously described, different instrument responses were attributed to changes in the instrument. However the described calibration transfer techniques can readily be applied to the situation in which the changes in instrument response are attributable to the differences between two or more groups. To apply the direct, classical, piecewise, and inverse models to such a situation, one simply makes the correspondence of reference instrument to one group of samples, and target instrument to the other group of samples, it being understood that the instruments may in fact be identical. In this case, for example for the direct technique, the transfer data converts a response measured for a sample in one (target) group into the response that would be measured for an otherwise identical sample from the other (reference) group.

The embodiments of the invention in which an exclusive property or privilege is claimed are defined as follows:

1. A method of producing a multivariate prediction model for predicting a property of a sample using a target spectrometer, based in part upon data measured by a reference spectrometer, the method comprising:

producing property data by measuring said property for each of a plurality of calibration samples;

for each calibration sample, producing a reference spectrometer response by making a plurality of measurements using the reference spectrometer;

for each transfer sample in a subset of the calibration samples, producing a target spectrometer response by making a plurality of measurements using the target spectrometer;

using the reference spectrometer responses for the calibration samples, the target spectrometer responses for the transfer samples, and the property data, producing estimates of the responses of the target spectrometer to the calibration samples; and producing a multivariate prediction model for the target spectrometer by combining the estimates of the responses of the target spectrometer to the calibration samples with the property data.

2. The method of claim 1, comprising the further steps of producing a target spectrometer response for an unknown sample using the target spectrometer, and predicting said property for the unknown sample by combining the multivariate prediction model for the target spectrometer with the target spectrometer response for the unknown sample.

3. The method of claim 1, wherein the step of producing estimates comprises determining $$R_1 + CC^{-+}(\bar{R}_2 - \bar{R}_1)$$

where $R_1$ is a matrix formed from the reference spectrometer responses for the calibration samples, $\bar{R}_1$ is a matrix formed from the reference spectrometer responses for the transfer samples, $\bar{R}_2$ is a matrix formed from the target spectrometer responses for the transfer samples, C is the property data for the calibration samples, and $C^{-+}$ is the pseudoinverse of a matrix formed from the property data for the transfer samples.

4. The method of claim 3, comprising the further steps of producing a target spectrometer response for an unknown sample using the target spectrometer, and predicting said property for the unknown sample by combining the multivariate prediction model for the target spectrometer with the target spectrometer response for the unknown sample.

5. A method of producing a multivariate prediction model for predicting a property of a sample using a target spectrometer, based in part upon data measured by a reference spectrometer, the method comprising:

producing property data by measuring said property for each of a plurality of calibration samples;

for each calibration sample, producing a reference spectrometer response making a plurality of measurements using the reference spectrometer;

for each transfer sample in a subset of the calibration samples, producing a target spectrometer response by making a plurality of measurements using the target spectrometer;

producing a multivariate prediction model for the reference spectrometer by using the reference spectrometer responses for the calibration samples the property data; and using the reference spectrometer responses for the transfer samples, the target spectrometer responses for the transfer samples, the multivariate prediction model for the reference spectrometer, and the property data, producing a multivariate prediction model for the target spectrometer.

6. To the method of claim 5, comprising the further steps of producing a target spectrometer response for an unknown sample by using the target spectrometer, and predicting said property for the unknown sample by combining the multivariate prediction model for the target spectrometer with the target spectrometer response for the unknown sample.

7. The method of claim 5, wherein the multivariate prediction model for the target spectrometer is determined as follows $$b_1 + (\bar{R}_2^+ - \bar{R}_1^+)c^-$$

where $b_1$ is the multivariate prediction model for the reference spectrometer, $\bar{R}_1+$ is the inverse of a matrix formed from the reference spectrometer responses for the transfer samples, $\bar{R}_2+$ is the inverse of a matrix formed from the target spectrometer responses for the transfer samples, and $c^-$ is a matrix formed from the property data for the transfer samples.

8. The method of claim 7, comprising the further steps of producing a target spectrometer response for an unknown sample using the target spectrometer, and predicting said property for the unknown sample by combining the multivariate prediction model for the target spectrometer with the target spectrometer response for the unknown sample.

9. A method of using a target spectrometer to perform a plurality of measurements on an unknown sample so as to produce an estimate of a reference spectrometer response for the unknown sample, the reference spectrometer response comprising values that would have been obtained by performing said plurality of measurements on the unknown sample using a reference spectrometer, the method comprising:

providing a plurality of transfer samples;

producing a reference spectrometer response for each transfer sample, by making a plurality of measurements using the reference spectrometer;

producing a target spectrometer response for each transfer sample, by making a plurality of measurements using the target spectrometer;

producing transfer coefficients for performing a multivariate estimation of the reference spectrometer responses for the transfer samples from the target spectrometer responses for the transfer samples;

producing a target spectrometer response for the unknown sample, by making a plurality of measurements using the target spectrometer; and converting the target spectrometer response for the unknown sample into an estimate of the reference spectrometer response for the unknown sample, using the transfer coefficients.

10. The method of claim 9, wherein each reference spectrometer response comprises a reference data value for each of M measurements made using the reference spectrometer, wherein each target spectrometer response comprises a target data value for each of M measurements made using the target spectrometer, and wherein the transfer coefficients comprise a plurality of estimation coefficients for estimating each reference data value from a window comprising a plurality of substantially less than M target data values.

11. The method of claim 10, wherein each reference spectrometer response includes one or more nonlinear functions of the measurements made using the reference spectrometer, and wherein each target spectrometer response includes the same nonlinear functions of the measurements made using the target spectrometer.

12. The method of claim 9, wherein the transfer coefficients F are produced by determining:

$$F = \bar{R}_2^+ \bar{R}_1$$

where $\bar{R}_2^+$ is the inverse of a matrix formed from the target spectrometer responses for the transfer samples of $\bar{R}_1$ is a matrix formed from the reference spectrometer response for the transfer samples.

13. The method of claim 9, wherein each reference spectrometer response and each target spectrometer response comprises a spectrum comprising a plurality of absorbance values at a corresponding plurality of wavelengths.

14. The method of claim 9, wherein the target spectrometer and the reference spectrometer are different spectrometers.

15. The method of claim 14, wherein each reference spectrometer response comprises a reference data value for each of M measurements made using the reference spectrometer, wherein each target spectrometer response comprises a target data value for each of M measurements made using the target spectrometer, and wherein the transfer coefficients comprise a plurality of estimation coefficients for estimating each reference data value from a window comprising a plurality of substantially less than M target data values.

16. The method of claim 14, wherein the transfer coefficients F are produced by determining $$F = \bar{R}_2^+ \bar{R}_1$$

where $\bar{R}_2^+$ is the pseudoinverse of a matrix formed from the target spectrometer responses for the transfer samples and $\bar{R}_1$ is a matrix formed from the reference spectrometer responses for the transfer samples.

17. The method of claim 9, comprising the further steps of:

providing a plurality of calibration samples, the calibration samples including the transfer samples plus additional samples;

producing a reference spectrometer response for each calibration sample, by making a plurality of measurements using the reference spectrometer;

producing property data by measuring a property for each calibration sample;

producing a multivariate prediction model for the reference spectrometer, using the reference spectrometer responses for the calibration samples and the property data; and predicting said property for the unknown sample by combining the estimate of the reference spectrometer response for the unknown sample with the multivariate prediction model for the reference spectrometer.

18. The method of claim 17, wherein said property is a concentration of an analyte included in the calibration samples.

\* \* \* \* \*